US008546076B2

(12) United States Patent (10) Patent No.: US 8,546,076 B2
Dierynck et al. (45) Date of Patent: Oct. 1, 2013

(54) MUTATIONAL PROFILE IN HIV-1 GAG CLEAVAGE SITE CORRELATED WITH PHENOTYPIC DRUG RESISTANCE

(75) Inventors: Inge Dierynck, Berchem (BE); Sandra De Meyer, Beerse (BE)

(73) Assignee: Tibotec Pharmaceuticals Ltd., Little Island, Co.Cork (IE)

( * ) Notice: Subject to any disclaimer, the term of this patent is extended or adjusted under 35 U.S.C. 154(b) by 0 days.

(21) Appl. No.: 13/529,324

(22) Filed: Jun. 21, 2012

(65) Prior Publication Data

US 2012/0258448 A1   Oct. 11, 2012

Related U.S. Application Data

(62) Division of application No. 12/601,483, filed as application No. PCT/EP2008/056356 on May 23, 2008, now abandoned.

(30) Foreign Application Priority Data

May 25, 2007 (EP) .................... 07108899

(51) Int. Cl.
*C12Q 1/70* (2006.01)
*C12Q 1/68* (2006.01)

(52) U.S. Cl.
USPC .............. 435/5; 435/6.1; 435/6.12

(58) Field of Classification Search
None
See application file for complete search history.

(56) References Cited

U.S. PATENT DOCUMENTS

2004/0265320 A1   12/2004   Salzwedel et al.

FOREIGN PATENT DOCUMENTS

| EP | 1605064 A1 | 12/2005 |
|---|---|---|
| WO | WO 97/27480 A1 | 7/1997 |
| WO | WO 00/73511 A1 | 12/2000 |
| WO | WO 00/78996 A1 | 12/2000 |
| WO | WO 01/79540 A2 | 10/2001 |
| WO | WO 02/22076 A2 | 3/2002 |
| WO | WO 02/22076 A3 | 3/2002 |
| WO | WO 02/33402 A2 | 4/2002 |
| WO | WO 02/33402 A3 | 4/2002 |
| WO | WO 02/38792 A2 | 5/2002 |
| WO | WO 02/38792 A3 | 5/2002 |

OTHER PUBLICATIONS

Bally et al. Polymorphism of HIV Type 1 Gag p7/p1 and p1/p6 Cleavage Sites: Clinical Significance and Implications for u Resistance to Protease Inhibitors. AIDS Research and Human Retroviruses 2000, vol. 16, No. 13, pp. 1209-1213.

Clotet et al., "Efficacy and safety of darunavir-ritonavir at week 48 in treatment-experienced patients with HIV-1 infection in POWER 1 and 2: a pooled subgroup analysis of data from two randomized trials", The Lancet, Lancet Limited, London GB, vol. 369, No. 9568, Apr. 6, 2007, 1169-1178.

D'Aquila, R. T., "HIV-1 Chemotherapy and Drug Resistance", Clin. Diagnost. Virol., vol. 3, 1995, 299-316.

De Oliveria Tulio et al., "Variability at human immunodeficiency virus type 1 subtype C protease cleavage sites: An indication of viral fitness?", Journal of virology, vol. 77, No. 17, Sep. 2003, 9425-9427.

Eastman, P. E., et al., "Nonisotopic Hybridization Assay for Determination of Relative Amounts of Genotypic Human Immunodeficiency Virus Type 1 Zidovudine Resistance", J. Clin. Micro., vol. 33, Oct. 1995, 2777-2780.

Eastman, P. S., et al., "Comparison of Selective Polymerase Chain Reaction Primers and Differential Probe Hybridization of Polymerase Chain Reaction Products for Determination of Relative Amounts of Codon 215 Mutant and Wild-Type HIV-1 Populations", J. Acquired. Immune. Deficiency. Syndromes and Human Retrovirology, vol. 9, 1995, 264-273.

Fodor, S.P.A. et al., "Multiplexed Biochemical Assays with Biological Chips", Nature, vol. 364, Aug. 1993, 555-556.

Fodor, S.P.A., "Massively Parallel Genomics", Science vol. 227, No. 5324, Jul. 1997, pp. 393-395.

Gingeras, T. R., et al., "Use of Self-Sustained Sequence Replication Amplification Reaction to Analyze and Detect Mutations in Zidovudine-Resistant Human Immunodeficiency Virus", J. Invect. Dis. vol. 154, Jul. 1991, 1066-1074.

Holodniy, M., et al., "Determination of Human Immunodeficiency Virus RNA in Plasma and Cellular Viral DNA Denotypic Zidovudine Resistance and Viral Load During Zidovudine-Didanosine Combination Therapy", J. Virology, vol. 69, Jun. 1995, 3510-3516.

Kaufmann, G.R. et al., "Impact of HIV type 1 protease, reverse transcriptase, cleavage site and p6 mutations on the virological response to quadruple therapy with saquinavir, ritonavir and two nucleoside analogs", AIDS Research and Human Retroviruses, vol. 17, No. 6, Apr. 10, 2001, 487-497.

Larder, B.A. et al., "HIV with Reduced Sensitifity to Zidovudine (AZT) Isolated During Prolonged Therapy", Science, vol. 243, Mar. 1989, 1731-1734.

Larder, B.A. et al., "Zidovudine resistance predicted by direct detection of mutations in DNA from HIV-infected lymphocytes", AIDS, vol. 5, 1991, 137-144.

(Continued)

*Primary Examiner* — Louise Humphrey
(74) *Attorney, Agent, or Firm* — Woodcock Washburn LLP

(57) ABSTRACT

The invention concerns novel mutations or mutational profiles of HIV-1 protease cleavage sites (CS) in the Gag region correlated with a phenotype causing alterations in sensitivity to anti-HIV drugs. The present invention also relates to the use of genotypic characterization of a target population of HIV and the subsequent association, i.e., correlation, of this information to phenotypic interpretation in order to correlate virus mutational profiles with drug resistance. The invention further relates to methods of utilizing the mutational profiles of the invention in databases, drug development, i.e., drug design, and drug modification, therapy and treatment design and clinical management.

7 Claims, No Drawings

(56) References Cited

OTHER PUBLICATIONS

Richman, D.D., et al, "Detection of Mutations Associated with Zidovudine Resistance in Human Immunodeficiency Virus by Use of the Polymerase Chain Reaction", J. Invect. Dis. vol. 164, Jul. 1991, 1075-1081.

Schinazi, Mutations in Retroviral Genes Associated with Drug Resistance: 2000-2001 update, Int. Antiviral News, vol. 6, 2000, 65-91.

Stuyver, L., et al., "Line Probe Assay for rapid detection of drug-selected mutations in the human immunodeficiency virus type 1 reverse transcriptase gene", Antimicrobial Agents Chemotherapy, vol. 41, Feb. 1997, 284-291.

Verheyen Jens et al., "Compensatory mutations at the HIV cleavage sites p7/p1 and p1/p6-gag in therapy-naïve and therapy-experienced patients", Antiviral Therapy, vol. 11, No. 7, 2006, 879-887.

Zhang Y-M et al., "Drug resistance during indinavir therapy is caused by mutations in the protease gene and in its gag substrate cleavage sites", Journal of virology, the American Society for Microbiology, vol. 71, No. 9, 1997, 6662-6670.

MUTATIONAL PROFILE IN HIV-1 GAG CLEAVAGE SITE CORRELATED WITH PHENOTYPIC DRUG RESISTANCE

CROSS-REFERENCE TO RELATED APPLICATIONS

The present application is a divisional of U.S. Ser. No. 12/601,483, filed Nov. 23, 2009 as the United States National Phase of PCT International Application No. PCT/EP2008/056356 filed May 23, 2008, which claims priority from European Application No. 07108899.1, filed May 25, 2007, the entire contents of each of which are incorporated herein by reference.

The present invention is directed to the field of nucleic acid diagnostics and the identification of base variation in target nucleic acid sequences. The invention provides novel mutations or mutational profiles of HIV-1 protease cleavage sites (CS) in the Gag region correlated with a phenotype causing alterations in sensitivity to anti-HIV drugs. The present invention also relates to the use of genotypic characterization of a target population of HIV and the subsequent association, i.e. correlation, of this information to phenotypic interpretation in order to correlate virus mutational profiles with drug resistance. The invention further relates to methods of utilizing the mutational profiles of the invention in databases, drug development, i.e., drug design, and drug modification, therapy and treatment design and clinical management.

The main target cell for HIV infection was identified as the CD4+ subset of T-cells. In order to replicate, HIV first interacts with cells expressing the CD4 surface protein and co-receptor via binding through the gp120 envelope protein. Following fusion via the gp41 domain of the envelope, entry is achieved, the viral particle degraded and the RNA genome transcribed into double-stranded complementary DNA (cDNA). This genetic material is transported into the cell nucleus as part of the pre-integration complex, where the DNA is processed by viral integrase and incorporated into the host genome. In an activated cell, the viral genome is transcribed and subsequently translated into structural proteins and enzyme precursors. The polypeptides, Gag and Gag-Pol containing matrix, capsid, nucleocapsid as well as the enzymes reverse transcriptase, protease and integrase are directed to the cell membrane where proteolytic cleavage by viral protease and virion packaging occurs. Most of these events have been extensively studied and a number of stages for possible intervention to prevent viral replication have been identified. These include attachment and entry into the host cell, formation of proviral DNA by reverse transcriptase enzymes, integration of proviral DNA into the host cell chromosomes by integrase, as well as virus assembly, including cleavage of the precursor viral proteins, by viral protease. Clinically relevant agents have been developed against two of these target stages reverse transcription (reverse transcriptase inhibitors (RTI)) and viral assembly (protease inhibitors (PI)). In addition, clinically relevant agents have been developed against fusion/entry of HIV into host cells, but also integrase inhibitors are in clinical development.

Protease Inhibitors (PIs) are peptidomimetics and bind to the active site of the viral protease enzyme, thereby inhibiting the cleavage of precursor polyproteins necessary to produce the structural and enzymatic components of infectious virions. Some PIs currently available include saquinavir (SQV), ritonavir (RTV), indinavir (IDV) nelfmavir (NFV), amprenavir (APV) and darunavir (DRV).

The options for antiretroviral therapy have improved considerably as new agents have become available. Current guidelines for antiretroviral therapy recommend a triple combination therapy regimen for initial treatment, such as one PI and 2 NRTIs (nucleoside reverse transcriptase inhibitor) or one NNRTI (non-nucleoside reverse transcriptase inhibitor) and 2 NRTIs. These combination regimens show potent antiretroviral activity and are referred to as HAART (highly active antiviral therapy). The introduction of HAART has resulted in a significant reduction of morbidity and mortality in HIV-1 patient populations with access to these drugs.

The development and standardization of plasma HIV-1 RNA quantification assays has led to the use of viral load measurements as a key therapy response-monitoring tool. The goal of antiretroviral therapy is to reduce plasma viremia to below the limit of detection on a long-term basis. However, in a significant number of patients, maximal suppression of virus replication is not achieved and for those in whom this goal is reached, a significant number experience viral load rebound. Viral load data provide no information on the cause of the failure.

Therapy failure may be due to a number of factors, including insufficient antiviral activity of the regimen, individual variations in drug metabolism and pharma-codynamics, difficulties in adhering to dosing regimen, requirements for treatment interruption due to toxicity, and viral drug resistance. Moreover, drug resistance may develop in a patient treated with sub-optimal antiretroviral therapy or a patient may be infected with drug-resistant HIV-1. Although drug resistance may not be the primary reason for therapy failure, in many cases any situation, which permits viral replication in the presence of an inhibitor, sets the stage for selection of resistant variants.

Viral drug resistance can be defined as any change in the virus that improves replication in the presence of an inhibitor. HIV-1 drug resistance was first described in 1989 and involved patients that had been treated with zidovudine monotherapy (Larder, B. A., et al., Science 243, 1731-1734 (1989)).

Emergence of resistance is almost always being observed during the course of treatment of patients with single antiretroviral drugs. Similarly, in vitro passage of viral cultures through several rounds of replication in the presence of antiretroviral compounds leads to the selection of viruses whose replication cycle is no longer susceptible to the antiretroviral compounds used. Resistance development has also been observed with the introduction of dual NRTI combination therapy as well as during the administering of the more potent NNRTIs, PIs and combinations thereof. Individual antiretroviral agents differ in the rate at which resistance develops: selection for resistant variants may occur within weeks of treatment or resistance may emerge after a longer treatment period.

Extensive genetic analysis of resistant viral isolates generated through in vivo or in vitro selection has revealed that resistance is generally caused by mutations at some specific site(s) of the viral genome. The mutational patterns that have been observed and reported for HIV-1 and that are correlated with drug resistance are very diverse: some antiretroviral agents require only one single genetic change, while others require multiple mutations for resistance to appear. A summary of mutations in the HIV genome correlated with drug resistance has been compiled (See e.g. Schinazi, Int. Antiviral News. 6, 65 (2000)). Electronic listings with mutations are available at different web locations.

A genetic mutation is normally written in reference to the wild type virus, i.e., K101N refers to replacement of a Lysine at codon 101 with a Asparagine (The Molecular biology of the Cell, 1994, Garland Publishing, NY).

The degree of susceptibility of a genetic variant to an antiretroviral compound is expressed herein relative to the wild-type virus (HIV IIIB/LAI reference sequence) as found, for example, in GenBank, the sequence of which is hereby incorporated by reference (K03455, gi 327742, M38432).

An alteration in viral drug sensitivity is defined as a change in resistance or a change in susceptibility of a viral strain to said drug. Susceptibilities are generally expressed as ratios of $EC_{50}$ or $EC_{90}$ values (the $EC_{50}$ or $EC_{90}$ value being the drug concentration at which 50% or 90% respectively of the viral population is inhibited from replicating) of a viral strain under investigation compared to the wild type strain. Hence, the susceptibility of a viral strain can be expressed as a fold change in susceptibility, wherein the fold change is derived from the ratio of for instance the $EC_{50}$ values of a mutant viral strain compared to the wild type. In particular, the susceptibility of a viral strain or population may also be expressed as resistance of a viral strain, wherein the result is indicated as a fold increase in $EC_{50}$ as compared to wild type $EC_{50}$.

As antiretroviral drugs are administered for longer periods, mostly in combination with each other, and as new antiretrovirals are being developed and added to the present drugs, new resistance-correlated genetic variants are being identified. Of particular importance is that the combination of antiretroviral agents can influence resistance characteristics.

Moreover, once viral resistance has developed, salvage therapy options may be severely restricted due to cross-resistance within each drug class. Based on models of virus replication dynamics and mutation rates, it would appear that a shift to mutant (resistant) virus population under conditions of incomplete suppression of viral replication in the presence of inhibitors is only a matter of time. Thus a key factor in preventing resistance, is maintaining complete (maximal) suppression of virus replication.

In view of the prevalence of viral resistance and its role in therapy failure, prevention of resistance development must be a key goal in the management of antiretroviral therapies. Recently, interest has been focused on the characterization of alterations in viral drug susceptibility for better clinical management. Given the significant role played by the existence and the continued evolution of resistance to antiretroviral drugs, the right choice for treatment regimen is very important. This is as important for initial treatment as for when a therapy change is called for in order to minimize the emergence of resistance and improve the long-term prognosis of the patient. The choice of therapy regimen will be supported by knowledge of the resistance profile of the circulating virus population. Additionally, therapy combinations will have a greater chance of being effective if they include agents that have a demonstrated potential of suppressing a particular virus population. Thus, unnecessary side effects and costs associated with drugs that the patient's virus is resistant to, may be avoided. However, to date, the understanding of the correlation between mutations of HIV and drug resistance and the effect of multi-drug combinations on resistance characteristics to individual agents is insufficient to accomplish many of these goals.

To achieve these and other advantages, and in accordance with the purpose of the invention as embodied and broadly described herein, the present invention, in one aspect, provides a computer system directed by software wherein the software correlates the presence of at least one mutation in the HIV-1 protease cleavage sites in the Gag region (p7/p1 cleavage site) and a change in susceptibility of at least one strain of HIV-1 to a protease inhibitor, more specifically to the combination darunavir/ritonavir.

HIV-1 protease (PR) catalyses the proteolytic processing of the GAG and GAG-polymerase polyprotein precursors substrate giving rise to the mature structural and enzymatic viral proteins. GAG is expressed as a 55 kDa precursor and is cleaved at the level of 5 sites, p17/p24, p24/p2, p2/p7, p7/p1 and p1/p6, to produce the mature proteins matrix (MA, p17), capsid (CA, p24), p2, nucleocapsid (NC, p'7), p1 and p6. To obtain a mature particle, there is an absolute requirement for cleavage at each site. The initial cleavage of the 55 kDa GAG precursor by the viral PR takes place at p2/p7, followed by cleavage of secondary p1/p6 and p17/p24, and finally of tertiary p7/p1 and p24/p7.

Changes in the PR binding pocket lead to decreased binding of PR inhibitors (PIs) and hence resistance, as well as to decreased binding of the natural substrate, GAG and GAG-polymerase polyproteins, and thus affect virus replication. Mutations in the GAG polyprotein are generally believed to be compensatory changes that do not directly affect PR resistance but adapt the virus to the altered substrate binding pocket of the mutant enzyme. Mutations in the viral GAG polyprotein have been described, with mutations in the PR cleavage sites in GAG most commonly found in the p2/p7, p7/p1, and p1/p6 cleavage sites. These mutations have also been observed in antiretroviral therapy (ART)-naïve individuals, suggesting that they exist as natural polymorphisms.

A number of applications describe the occurrence of mutations in HIV and their correlation to the development of drug resistance (WO 00/73511; WO 02/33402; WO 02/22076; WO 00/78996). The instant invention adds to the art a mutation in the gag gene, more specifically in the HIV-1 protease cleavage sites in the gag-region (p7/p1 cleavage site) and its correlation i.e. association to viral drug resistance, more specifically to the combination darunavir/ritonavir.

Said correlation between the mutation and drug resistance is that if the HIV gag mutation is E428G, the HIV strain has a decreased susceptibility in combination with other gag and/or protease mutations to at least the combination of darunavir/ritonavir.

In another embodiment, the invention is drawn to a method of evaluating the effectiveness of antiretroviral therapy more specifically to the combination of darunavir and ritonavir of treatment experienced HIV patients comprising: collecting a sample from an HIV-infected patient; determining whether the sample comprises at least one nucleic acid sequence encoding HIV gag-pol region having at least one mutation E428G in the gag gene and using the presence of the nucleic acid sequence to evaluate the effectiveness of the antiviral therapy.

The invention also provides for a method of designing therapy for treating patients infected with HIV comprising: collecting a sample from an HIV-infected patient; determining whether the sample comprises at least one nucleic acid sequence encoding HIV gag-pol region having at least one mutation E428G in the gag gene described herein; and using the presence of the nucleic acid sequence to design a therapy for the patient.

In general a change in effectiveness can be expressed as a fold change in resistance. The fold change may be determined using a cellular assay including the cytopathogenic assay or the ANTIVIROGRAM® (WO 97/27480). Alternatively, the fold change in susceptibility may be derived from database analysis such as the VircoTYPE HIV-1™ (WO 01/79540). A decrease in susceptibility vis-à-vis the wild type virus correlates to an increased viral drug resistance, and hence reduced effectiveness of said drug. To determine the viral drug susceptibility the activity of the mutant enzyme may be compared to the activity of a wild type enzyme. In phenotyping assays pseudotyped viruses may be used. The mutations present in HIV gag-pol region may be determined at the nucleic acid or amino acid level using sequencing or hybridization techniques. A report may be generated that shows the region of the patient virus that has been sequenced, including at least one mutation E428G. The report may include antiretroviral drugs, drug(s) for which a known resistance-associated mutation has been identified and/or to what extent the observed mutation(s) selected from at least E428G are indicative of resistance to drugs. The sample to be evaluated can be a bodily fluid including blood, serum, plasma, saliva, urine, or a tissue including gut tissues.

A drug effective against a mutant in HIV gag-pol region may be identified by a method, comprising: (i) providing a nucleic acid sequence comprising HIV gag-pol region comprising at least one mutation E428G in the gag gene; (ii) determining a phenotypic response to said drug for said HIV recombinant virus; and (iii) identifying a drug effective against mutant HIV based on the phenotypic response of step (ii). The nucleic acid sequence comprising HIV of step (i) may be recombined into a proviral nucleic acid sequence deleted for said sequence to generate a recombinant HIV virus.

Identifying a drug is defined as making a selection of drugs clinically available based on the effectiveness of said drug. In addition to the selection of clinically available drugs identifying also relates to the selection of clinical drug candidates. The phenotypic response may be determined using cellular assays such as the ANTIVIROGRAM®. An effective drug against mutant HIV comprising at least one mutation E428G in the gag region or gag gene is defined as a drug having a phenotypic response expressed, as e.g. a fold change in susceptibility lower than a defined cut-off that may be determined for a drug.

Another useful method for identifying, a drug effective against a mutant in HIV gag-pol region comprises: (i) providing a HIV gag-pol region comprising at least one mutation E428G in the gag gene, (ii) determining the activity of said drug on said HIV gag-pol region; (iii) determining the activity of said drug on wild type HIV gag-pol region; (iv) determining the ratio of the activity determined in step (iii) over the activity determined in step (ii); (v) identifying an effective drug against the mutant HIV based on the ratio of step (iv).

A ratio lower than a defined cut-off value that can be specific for said drug is indicative that the drug is effective against mutant HIV (WO 02/33402).

EXPERIMENTAL PART

Genotyping Methodologies

Resistance of HIV to antiretroviral drugs may be determined at the genotypic level by identifying mutations in the HIV-1 genome and by inferring the resistance of HIV-1 to antiretroviral drugs through searching for mutational patterns known to correlate with resistance. Assays for detection of mutations in HIV-1 may be based on polymerase chain reaction (PCR) amplification of viral genomic sequences. These amplified sequences are then analyzed using either hybridization or sequencing techniques. Hybridization-based assays include primer-specific PCR, which makes use of synthetic oligonucleotides designed to allow selective priming of DNA synthesis. See Larder, B. A., et al., AIDS 5, 137-144 (1991); Richman, D. D., et al., J. Infect. Dis. 164, 1075-1081 (1991); Gingeras, T. R., et al., J. Infect. Dis. 164, 1066-1074 (1991). Only when primer sequences match the target sequence (wild-type or mutant) at the 3' end, is amplification of target sequences possible and DNA fragments are produced. Knowledge of the primer sequences allows one to infer the sequence of the viral isolate under investigation, but only for the region covered by the primer sequences. Other hybridization-based assays include differential hybridization (Eastman, P. S., et al., J. Acq. Imm. Def. Syndr. Human Retrovirol. 9, 264-273 (1995); Holodniy, M., et al., J. Viral. 69, 3510-3516 (1995); Eastman, P. S., et al., J. Clin. Micro. 33, 2777-2780 (1995).); Line Probe Assay (LiPAJ HIV-11 RT, Innogenetics) (Stuyver, L., et al., Antimicrob. Agents Chemotherap. 41, 284-291 (1997)); and biochip technology such as GENECHIP® technology (Affymetrix) (D'Aquila, R. T. Clin. Diagnost. Virol. 3, 299-316 (1995); Fodor, S. P. A. et al., Nature 364, 555-556 (1993); Fodor, S. P. A. Nature 227, 393-395 (1997). The sequence may also be determined using mass spectroscopic technologies. DNA sequencing assays provide information on all nucleotides of the sequenced region.

Phenotyping Methodologies

Phenotyping assays measure the ability of a replicating virus to grow in the presence of compounds compared to a wild-type reference virus such as e.g. HIV-1/LAI, HIV-1/NL4.3, HIV-1/HXB2 or e.g. HIV-2/ROD. Alternatively, phenotyping assays are performed with pseudotyped viruses not able to replicate (WO 02/38792). Consequently, these assays directly measure the degree of viral susceptibility to specific inhibitors. In this case, one measures the effect of all mutational interactions, the effects of genetic changes as yet unknown or not previously identified, the effect of the background genotype, etc., on the phenotype.

Impact of Gag Cleavage Site (CS) Mutations on the Virologic Response to Darunavir/Ritonavir in Treatment-Experienced Patients Pooled data of treatment-experienced subjects who initiated darunavir/ritonavir treatment at the recommended dose of 600/100 mg twice daily (N=467) with an optimized background regimen were analyzed in a univariate analysis. Virologic response was defined as viral load ≤50 copies/mL at week 24. Mutations in the 5 Gag CS were determined at baseline and confirmed point of rebound and/or a later time point within the treatment phase.

Among the CS mutations present in >10 patients at baseline only E428G was surprisingly linked with a reduced virologic response to darunavir/ritonavir at week 24 (<75% of overall response).

Study Population

GAG genotypic analysis was performed on virus isolates from subjects of pooled trials. All subjects included in the Week 96 efficacy analysis and Week 48 efficacy analysis of said trails, who received the recommended dose of DRV/rtv 600/100 mg b.i.d. starting from Day 1, were included in this analysis.

Virological failures were defined using the TLOVR non-virologic failure (VF)-censored algorithm in which the responses at time points after discontinuation are not imputed (i.e. left missing) for patients who drop for reasons other than virologic failures. Using this imputation, patients that drop out for reasons other than viro logic failure are not automatically considered as rebounders or non-responders. Additionally, patients who did not have the chance to respond (patients who did not have data in the Week 16 slotted window or thereafter) were not taken into account to determine rebound or non-response.

Genotypic Analysis

Genotypic analyses were performed by automated population-based sequencing. Sequence data were aligned to the wildtype HIV-1/HXB2$_{CG}$ reference and reported as amino acid changes along GAG and PR. Genotypic mixtures (a combination of different amino acids at 1 position) were reported. Amino acids were presented with their one letter code. Mutations in the 5 PR cleavage sites in the GAG region, encompassing the amino acids 128-137 (p17/p24), 359-368 (p24/p2), 373-382 (p2/p7), 428-437 (p7/p1), and 444-453 (p1/p6), were reported.

Genotypes (PR and reverse transcriptase [RT]) were determined by default on plasma samples taken at predefined time points (e.g. screening, Week −2, baseline, Week 2, Week 24, Week 48, Week 96, Week 144 and final/withdrawal visit) when the viral load was >1000 HIV-1 RNA copies/mL. Furthermore, samples at other time points, such as confirmed virologic failure, were also analyzed upon request of the protocol virologist. GAG genotypic analysis was determined at baseline and confirmed point of rebound and/or a later time point within the treatment phase.

Identification of Developing Mutations

Development of a mutation was defined as an amino acid substitution that could be detected at endpoint but not at baseline by genotypic analysis (population-based sequencing). Endpoint could be a time point pre-defined in the protocol to perform a genotype or a time point at which a genotype was requested by the protocol virologist, e.g. at the time of virologic failure.

Mutations Listings Used

The International AIDS Society (IAS)-USA Drug Resistance Mutation list, updated in 2006 was used for analyses of mutations in the PR.

Phenotypic Analysis

Recombinant HIV-1 clinical isolates were constructed according to the ANTIVIROGRAM® method. Briefly, PR and RT coding sequences were amplified from patient-derived viral RNA with HIV-1 specific primers. After homologous recombination of amplicons into a PR-RT deleted proviral clone, the resulting recombinant viruses were harvested and used for in vitro susceptibility testing.

Influence of Genotype on Response

Virologic response was defined using the TLOVR non-VF censored algorithm eliminating patients who had no chance to respond (discontinuation before Week 16). Several endpoints to assess virologic response, e.g. proportion of responders with confirmed 1.0 $\log_{10}$ decrease in viral load versus baseline, change in viral load from baseline (NC=F), and proportion of responders with viral load <50 or <400 HIV-1 RNA copies/mL were evaluated.

Influence of Baseline GAG Genotype on Response to DRV/rtv Treatment

Analyses of virologic outcome at Week 24 by baseline GAG genotype were based on the studied population of subjects from the trials that received the recommended dose of DRV/rtv 600/100 mg b.i.d (N=467). Virologic response was defined using the TLOVR, non-VF censored algorithm eliminating patients who had no chance to respond (discontinuation before Week 16), resulting in 445 subjects included in the analysis. To assess outcome, several endpoints including the primary endpoint (proportion of responders with confirmed 1.0 $\log_{10}$ decrease in viral load at Week 24), change in viral load from baseline at Week 24 and proportion of responders with viral load <50 HIV-1 RNA copies/mL at Week 24 were evaluated. In addition, virologic outcomes were examined in 3 separate groups: all subjects (All), subjects who did not use ENF (enfuvirtide) or who used ENF currently and received ENF in their previous therapy (no/non-naïve ENF), and subjects who started ENF for the first time (ENF naïve) in the trials. The focus was on the no/non-naïve ENF group to assess baseline resistance predictors of response to DRV/rtv treatment without the additive effect of ENF use.

The influence of the presence at baseline of PR cleavage site mutations in GAG on the response to DRV/rtv at Week 24 was studied. All subjects from the trials in the studied population, who had received DRV/rtv 600/100 mg b.i.d. in their initial regimen were clustered in subpopulations on the basis of the presence of each PR cleavage site mutation in GAG occurring at baseline. Only mutations present at baseline in 10 subjects of the no/non-naïve ENF group (N=327) were taken into consideration. Virologic response was defined in 3 different ways (decrease of ≥1.0 $\log_{10}$ in plasma viral load versus baseline, change versus baseline in $\log_{10}$ viral load, or viral load <50 HIV-1 RNA copies/mL), and diminished response was defined as response rates <75% of the overall response rate or mean changes versus baseline in viral load <1.0 $\log_{10}$.

Response rate (TLOVR, non-VF censored) as a decrease of ≥1.0 $\log_{10}$ in plasma viral load versus baseline at week 24: for the subpopulations of subjects of the no/non-naïve ENF group with the PR cleavage site mutations in GAG E428G, and/or R452S at baseline, response rates of <48.8%, i.e. 75% or less of the overall response rate (65.1%), were observed. The lowest response rate (27.8%) was found when R452S was present at baseline; the presence of E428G at baseline still showed a response of 40% (Table 1).

Change versus baseline in log 10 viral load (NC=F, non-VF censored) at Week 24: for the subpopulations of subjects of the no/non-naïve ENF group with the PR cleavage site mutations in GAG E428G and/or R452S at baseline, mean changes versus baseline in viral load at Week 24<1.0 $\log_{10}$ were observed. The mean changes versus baseline in viral load were still >0.5 $\log_{10}$ in subjects of the no/non-naïve ENF subgroup (Table 2). In the other subgroups (All, naïve ENF), the mean changes were >1.0 $\log_{10}$.

Response rate (TLOVR, non-VF censored) as a viral load <50 HIV-1 RNA copies/mL at Week 24: for the subpopulations of subjects of the no/non-naïve ENF group with the PR cleavage site mutations in GAG E428G (15 subjects), L449P (21 subjects), S451T (14 subjects), and/or R452S (18 subjects) at baseline, response rates <32.3%, i.e. 75% or less of the overall response rate (43.1%) were observed. The smallest response rate (5.6%) was found when R452S was present at baseline; the presence of E428G, L449P and/or S451T at baseline showed a response rate of 13.3%, 28.6%, and 21.4%, respectively (Table 3). Two additional mutations (L449P and S451T) were identified with this more stringent response parameter compared to the other response parameters.

The baseline PR cleavage site mutations in GAG E428G and R452S, present in 4.3% and 5.6% of all subjects, respectively, were identified as leading to a reduced response by all 3 definitions of response.

TABLE 1

Virologic Response Rate (TLOVR, non-VF Censored) Defined as a Decrease ≥1.0 $\log_{10}$ in Plasma Viral Load Versus Baseline at Week 24 by Presence of Individual PR Cleavage Site Mutations in GAG at Baseline

| | DRV/rtv 600/100 mg b.i.d. | | |
|---|---|---|---|
| PR cleavage site mutation in GAG[a] (cleavage site) | All N n (%) | no/non-naïve ENF N n (%) | naïve ENF N n (%) |
| Overall | 445 315 (70.8) | 327 213 (65.1) | 118 102 (86.4) |

TABLE 1-continued

Virologic Response Rate (TLOVR, non-VF Censored) Defined
as a Decrease ≥1.0 $\log_{10}$ in Plasma Viral Load Versus
Baseline at Week 24 by Presence of Individual PR Cleavage
Site Mutations in GAG at Baseline

| | DRV/rtv 600/100 mg b.i.d. | | |
|---|---|---|---|
| PR cleavage site mutation in GAG[a] (cleavage site) | All N n (%) | no/non-naïve ENF N n (%) | naïve ENF N n (%) |
| E428G (p7/p1) | 19 9 (47.4) | 15 6 (40.0) | 4 3 (75.0) |
| R452S (p1/p6) | 25 12 (48.0) | 18 5 (27.8) | 7 7 (100) |

[a]When a mixture of different mutations was detected at a certain position, each individual mutation was taken into account for the calculation of the number of subjects showing that mutation at baseline.
All individual PR cleavage site mutations in GAG for which N ≥ 10 for the no/non-naïve ENF DRV/rtv group, and for which the virologic response rate (defined as a decrease ≥1.0 $\log_{10}$ in plasma viral load versus baseline [TLOVR, non-VF censored] at Week 24) is 75% or less of the overall response rate, i.e. 48.8%, are presented.
N = total number of subjects; n = number of responders

TABLE 2

Change versus Baseline in $\log_{10}$ Viral Load (NC = F,
non-VF Censored) at Week 24 (HIV-1 RNA copies/mL) by Presence
of Individual PR Cleavage Site Mutations in GAG at Baseline

| | DRV/rtv 600/100 mg b.i.d. | | |
|---|---|---|---|
| PR cleavage site mutation in GAG[a] (cleavage site) | All N Mean (SE) | no/non-naïve ENF N Mean (SE) | naïve ENF N Mean (SE) |
| Overall | 445 −1.84 (0.061) | 327 −1.67 (0.071) | 118 −2.33 (0.109) |
| E428G (p7/p1) | 19 −1.07 (0.298) | 15 −0.89 (0.318) | 4 −1.72 (0.763) |
| R452S (p1/p6) | 25 −1.12 (0.293) | 18 −0.58 (0.312) | 7 −2.50 (0.276) |

[a]When a mixture of different mutations was detected at a certain position, each individual mutation was taken into account for the calculation of the number of subjects showing that mutation at baseline. All individual PR cleavage site mutations in GAG for which N ≥ 10 for the no/non-naïve ENF DRV/rtv group, and for which the mean change in plasma viral load versus baseline (NC = F, non-VF censored) was <1.0 $\log_{10}$ at Week 24, are presented.
N = total number of subjects; n = number of responders, SE = standard error

TABLE 3

Virologic Response Rate (TLOVR, non-VF Censored) Defined as
a Viral Load <50 HIV-1 RNA copies/mL at Week 24 by Presence
of Individual PR Cleavage Site Mutations in GAG at Baseline

| | DRV/rtv 600/100 mg b.i.d. | | |
|---|---|---|---|
| PR cleavage site mutation in GAG[a] (cleavage site) | All N n (%) | no/non-naïve ENF N n (%) | naïve ENF N n (%) |
| Overall | 445 207 (46.5) | 327 141 (43.1) | 118 66 (55.9) |
| E428G (p7/p1) | 19 3 (15.8) | 15 2 (13.3) | 4 1 (25.0) |
| L449P (p1/p6) | 33 12 (36.4) | 21 6 (28.6) | 12 6 (50.0) |
| S451T (p1/p6) | 22 4 (18.2) | 14 3 (21.4) | 8 1 (12.5) |
| R452S (p1/p6) | 25 7 (28.0) | 18 1 (5.6) | 7 6 (85.7) |

[a]When a mixture of different mutations was detected at a certain position, each individual mutation was taken into account for the calculation of the number of subjects showing that mutation at baseline. All individual PR cleavage site mutations in GAG for which N ≥ 10 for the no/non-naïve ENF DRV/rtv group, and for which the virologic response rate (defined as a plasma viral load below 50 HIV-1 RNA copies/mL [TLOVR, non-VF censored] at Week 24) is 75% or less of the overall response rate, i.e. 32.3%, are presented.
N = total number of subjects; n = number of responders

What is claimed:

1. An assay for detecting an HIV infection characterized by decreased viral drug susceptibility comprising:
   collecting a sample from a patient infected with HIV; and
   utilizing a PCR assay comprising a primer targeting an E482G mutation in the gag gene, determining whether the sample comprises a HIV gag-pol having a mutation E428G in the gag gene,
   wherein the codon number of said E428G mutation corresponds to a wild type HIV IIIB/LAI reference sequence,
   wherein the presence of said mutation E428G is correlated with decreased viral drug susceptibility.

2. A method for evaluating the efficacy of a therapy regimen that includes a protease inhibitor against a mutant HIV in a subject, comprising:
   utilizing the assay according to claim 1, assessing whether said HIV comprises a mutation E428G in the gag gene; and,
   based on said assessment, either applying said therapy regimen to said subject or applying an alternative treatment that is different from said therapy regimen to said subject, wherein the presence of the mutation is correlated with decreased efficacy of the therapy regimen.

3. The method according to claim 2, wherein said therapy regimen includes the combination of duronavir and ritonavir.

4. The method according to claim 2, wherein said HIV includes at least one further mutation in the gag gene.

5. A method for evaluating viral drug susceptibility in a patient infected with HIV, comprising:
   assessing whether said HIV comprises a mutation E428G in the gag gene utilizing the assay according to claim 1; and,
   based on said assessment, either applying viral drug therapy to said patient or applying treatment to said patient that does not include viral drug therapy to which said HIV infection has decreased susceptibility.

6. The method according to claim 5 wherein said drug includes the combination of duronavir and ritonavir.

7. The method according to claim 5 wherein said HIV gag-pol includes at least one further mutation in the gag gene.

* * * * *